United States Patent [19]
Grandgenett

[11] Patent Number: 5,811,270
[45] Date of Patent: Sep. 22, 1998

[54] IN VITRO METHOD FOR CONCERTED INTEGRATION OF DONOR DNA MOLECULES USING RETROVIRAL INTEGRASE PROTEINS

[76] Inventor: Duane P. Grandgenett, 8610 Henrietta Ave., Brentwood, Mo. 63144

[21] Appl. No.: 671,071

[22] Filed: Jun. 27, 1996

Related U.S. Application Data

[63] Continuation of Ser. No. 247,089, May 20, 1994, abandoned.
[51] Int. Cl.[6] .............................. C12P 19/34; C12Q 1/68; C12N 15/10
[52] U.S. Cl. .......................... 435/91.1; 435/91.4; 435/6; 435/172.3
[58] Field of Search .......................... 435/6, 172.3, 91.1, 435/91.4

[56] References Cited

PUBLICATIONS

Fitzgerald et al. (1992) "Concerted Integration of Viral DNA Termini by Purified Avian Myeloblastosis Virus Integrase" J. Virol. 66:6257–6263.
Craigie et al. (1987) "Transposition of Mu DNA: Joining of Mu to Target DNA can be uncoupled from Cleavage at the end of Mu" Cell 51:493–501.

*Primary Examiner*—Jasemine C. Chambers
*Assistant Examiner*—Scott D. Priebe

[57] ABSTRACT

A method of analysis of concerted integration in which viral integrase enzyme is first incubated with donor DNA molecules followed by incubation with target DNA molecules. The donor DNA molecule having at least one unique restriction site for analysis of concerted integration product.

6 Claims, 12 Drawing Sheets

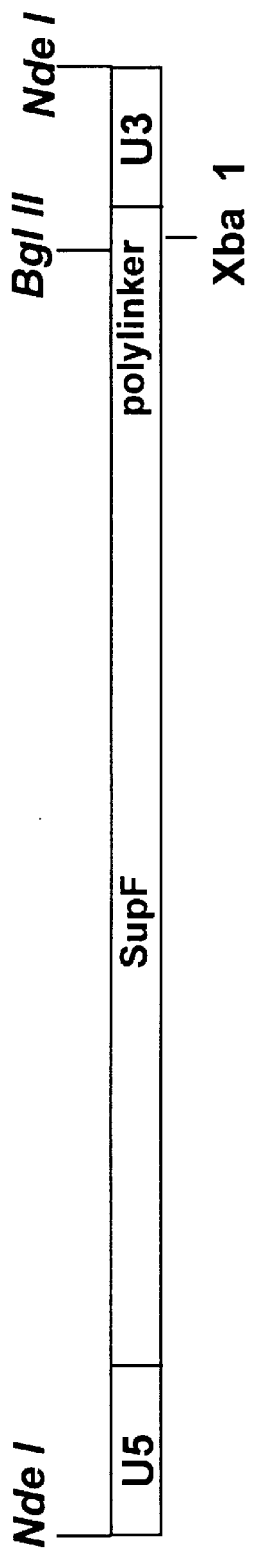
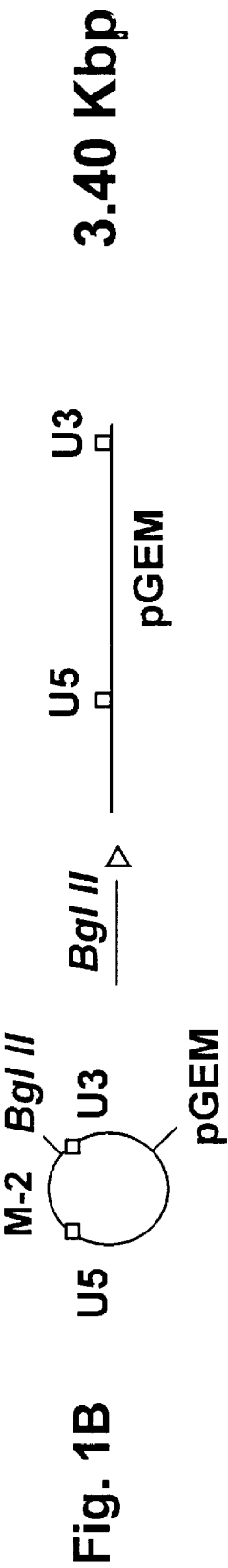
Fig. 1A
Fig. 1B

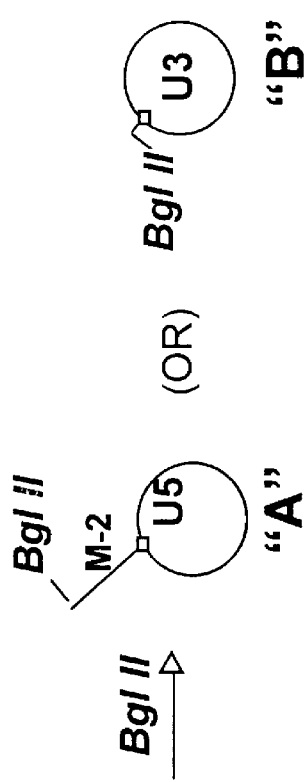
Fig. 1C
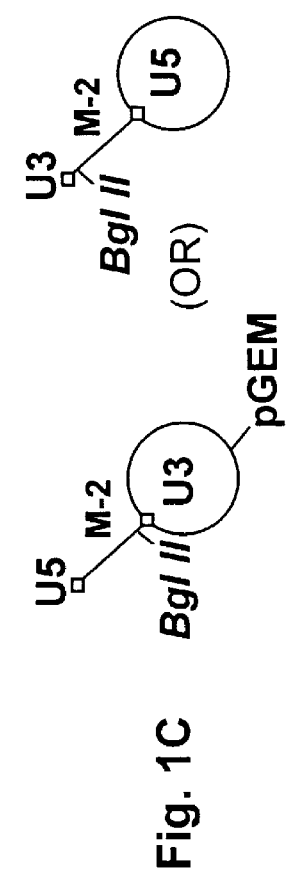
Fig. 1D

FIG. 14

```
                          M2
                 ┌─────────────────────┐
-CAGCCCAGTA                    ┌U3--CTACA┐  CCAGTAGTAG-
-GTCGGGTCAT  ┌ACTTC--U5┐                    GGTCATCATC-

M2
                 ┌─────────────────────┐
-TTACTCATAT                    ┌U3--CTACA┐  CTCATATATA-
-AATGAGTATA  ┌ACTTC--U5┐                    GAGTATATAT-

M2
                 ┌─────────────────────┐
-AAGGAATGGT                    ┌U3--CTACA┐  AATGGTGCAA-
-TTCCTTACCA  ┌ACTTC--U5┐                    TTACCACGTT-
```

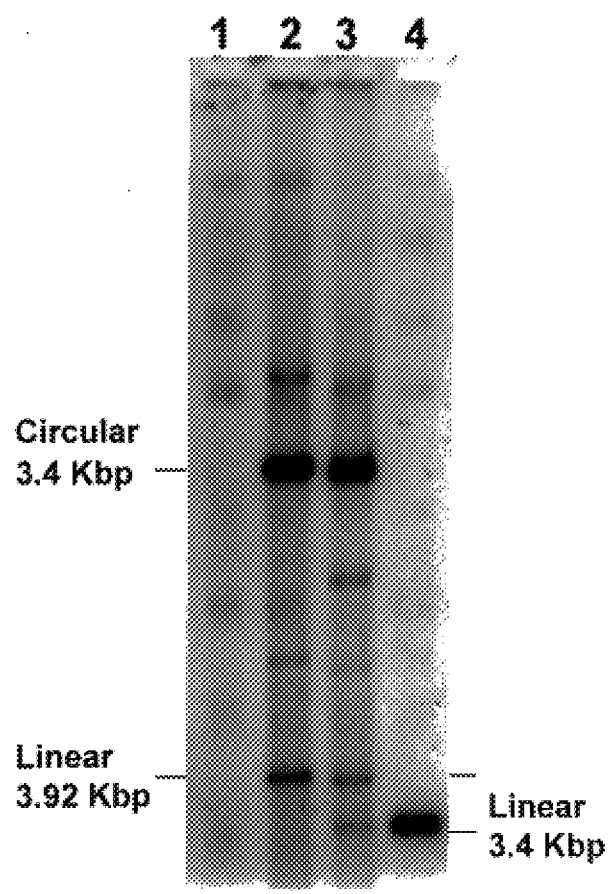

IN VITRO METHOD FOR CONCERTED INTEGRATION OF DONOR DNA MOLECULES USING RETROVIRAL INTEGRASE PROTEINS

This is a continuation of an earlier patent application Ser. No. 08/247,089 filing date May 20, 1994, now abandoned.

This invention was made with the U.S. Government support awarded by National Institute of Health. The U.S. Government may have certain rights in the invention.

BACKGROUND OF THE INVENTION

Upon infection of cells by retroviruses, a large-size viral nucleoprotein complex is observed in the cytoplasm. These complexes vary in size from 160 S for murine leukemia virus (MLV) to 80 S for human immunodeficiency virus (HIV) type-1. The viral nucleoprotein complexes contain newly synthesized blunt-ended linear viral DNA that is subsequently trimmed by two nucleotides at its 3' OH termini by the viral integrase(IN). IN can catalyze the concerted integration of the recessed viral DNA termini into exogenous DNA targets (full-site reaction) mimicking the in vivo reaction. Both the trimming and integration of the viral DNA by IN in the nucleoprotein complexes requires the metal cofactor $Mg^{2+}$.

Similar trimming and integration reactions can also be catalyzed by purified IN in vitro. IN derived from bacterial expression systems or purified from avian myeloblastosis virus (AMV) can trim two nucleotides from the termini of oligonucleotides or DNA restriction fragments containing viral long terminal repeat (LTR) sequences. The recessed DNA substrates can then be integrated into other DNA targets by IN. The majority of the observed integration events with these substrates involve the insertion of a single LTR terminus into one strand of the target DNA (half-site reaction). Expressed IN requires $Mn^{2+}$ for efficient catalysis of either the trimming or the strand transfer reactions while AMV IN can effectively use $Mg^{2+}$ or $Mn^{2+}$ for these reactions. To date, expressed IN is not capable of efficiently performing the concerted insertion of viral-like DNA substrates into target DNA using either divalent cation.

DESCRIPTION OF THE INVENTION

The present invention relates to a method and a kit for efficient integration of DNA donor molecules into DNA target molecules using retrovirus integrase, hereinafter referred to as IN. The present invention also relates to a method for studying integrase such as screening of HIV-1 or HIV-2 integrase inhibitors, production of transgenic animals and gene transfer.

According to the present invention, IN purified from virus or IN in virus particles and specifically designed donor substrates, hereinafter referred to as donor DNA, are used to mimic the integration of retrovirus DNA in vivo. This does not exclude the possibility that suitable expressed IN could perform concerted integration. The reaction assay conditions and donor DNA molecules being such that they induce a high cyclization probability for the donor DNA molecules in the reaction solution. Concerted integration of a single donor DNA requires the transient formation of a circle molecule prior to this event. The donor DNA molecules could also have regions capable of readily bending in solution and located appropriately to enhance cyclization of the donor DNA molecules in reaction solution. It should be understood that cyclization of donor DNA is necessary for the concerted integration of the two donor termini, in which each termini has a dimer of IN. Furthermore, the condition inducing cyclization may also be influenced by temperature, concentration of reactants, order of addition of reactants, and divalent metal cation.

The donor DNA molecules should have at least one unique restriction site for analysis of successful and efficient concerted integration. This analysis may be readily performed on agarose gels. Preferably, the donor DNA molecules have at least one genetic marker for isolation or characterization of concerted integration products.

Preferably, the donor DNA molecules can be labeled at their 5' ends, using radioactive probes but not excluding other detection probes.

For efficient concerted integration of a donor DNA molecule into a target molecule, IN and the donor DNA molecule are incubated in reaction buffer which allows formation of transient circles. Preferably, the reaction buffer contains 20 mM $MgCl_2$, 10% dimethyl sulfoxide, 0.05% Nonidet P-40, 5% polyethylene glycol, and 200 mM NaCl. After formation of transient circles of donor DNA with IN, the target molecule is introduced into the reaction and the integration reaction is allowed to proceed. After the integration reaction is complete, the reaction products may be analyzed for the unique restriction site and the genetic marker on the donor DNA molecule.

Preferably, the donor molecules should be of a optimum size for the cyclization of the DNA to occur in solution. The size can vary with certain DNAs but should be in the 700 bp range, with several hundred base pairs on either size. It should be understood that small size DNA molecules are too rigid for cyclization in assay solution while large size DNA molecules are too flexible for stable cyclization. DNA sequences that readily bend in solution may be introduced in the donor DNA thereby increasing the size of the donor that can be used because its cyclization frequency should be higher.

Preferably, the donor molecule should lack internal DNA sequences, such as A/T rich regions, that IN can readily bind to thereby lowering the concentration of IN in solution. Also, non-specific binding of IN to regions other then the donor termini would allow formation of DNA loop structures that inhibit the formation of transient circles by IN.

Preferably, the target DNA molecule for in vitro analysis should be a circle whose size could be easily varied. The circular target DNA and unique restriction site on the donor DNA molecules makes analysis of the concerted integration reaction easy by the use of gel electrophoresis. This invention could be readily applied to the study and identification of HIV-1 or HIV-2 IN inhibitors. HIV-1 virions can readily perform the concerted integration of the appropriate DNA donor that matches the size criteria stated above into a circular target.

Preferably, for the production of transgenics and for the practice of gene transfer, the donor molecule would be complexed with IN prior to their transfer into the animals or cells. As noted below, this formation of IN/donor preintegration complexes is the most efficient method to produce concerted integration recombinants with target DNA. In transgenics and gene transfer the host genome acts as the target DNA.

BRIEF DESCRIPTION OF THE DRAWINGS

The invention is further explained with reference to the following drawings:

FIG. 1. DNA structures and pathways involved in formation of M-2/pGEM recombinants. (A) The 528 bp M-2 molecule possesses the terminal 24 bp of the U3 LTR and 36 bp of the terminal U5 LTR, flanked by a NdeI site. The supF gene is located between the LTR termini. (B) Depicts the concerted integration( full-site) of a single M-2 molecule into circular pGEM. Bg/ll digestion produces a linear 3.4 Kbp DNA. (C) Half-site insertion of M-2 into pGEM in various orientations. Depending upon M-2 orientation into pGEM, Bg/ll digestion produces two ball and stick molecules. (D) Depicts the concerted integration of two separate M-2 molecules into the same pGEM site producing a linear 3.92 Kbp DNA. Four possible recombinant structures are possible. Bg/ll digestion results in the formation of four possible linear structures, with the two 3.4 Kbp structures comigrating.

Figure 2:
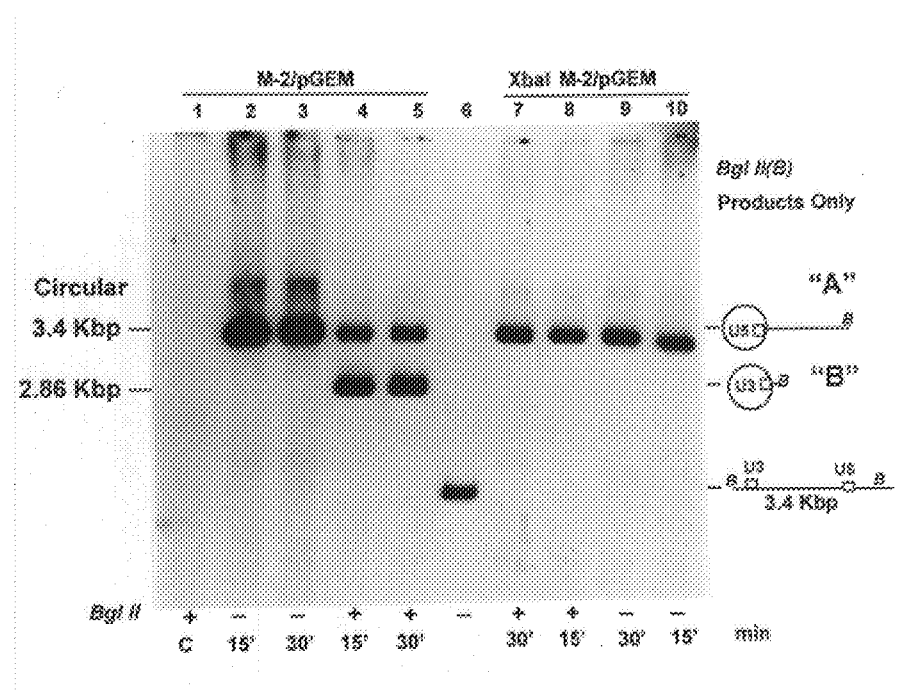

FIG. 2. Bg/ll restriction analysis of M-2/pGEM and XbaI cut M-2/pGEM recombinants. AMV IN, M-2( or slightly truncated M-2), and circular pGEM were preincubated together on ice prior to incubation at 37° C. for various times under standard conditions with $Mg^{2+}$ except that the donor to target molar ratio was 16 instead of 1. After processing and Bg/ll digestion, the samples were subjected to 1.5% agarose gel electrophoresis. The gel was dried and exposed for 34 hr. The left side identifies undigested products and the right side identifies Bg/ll digestion products. Lane 1 was a control lane with no added IN and lane 6 contained a 5' end-labeled linear 3.4 Kbp marker. The bottom indicates times of incubation and which samples were digested with Bg/ll.

Figure 3:
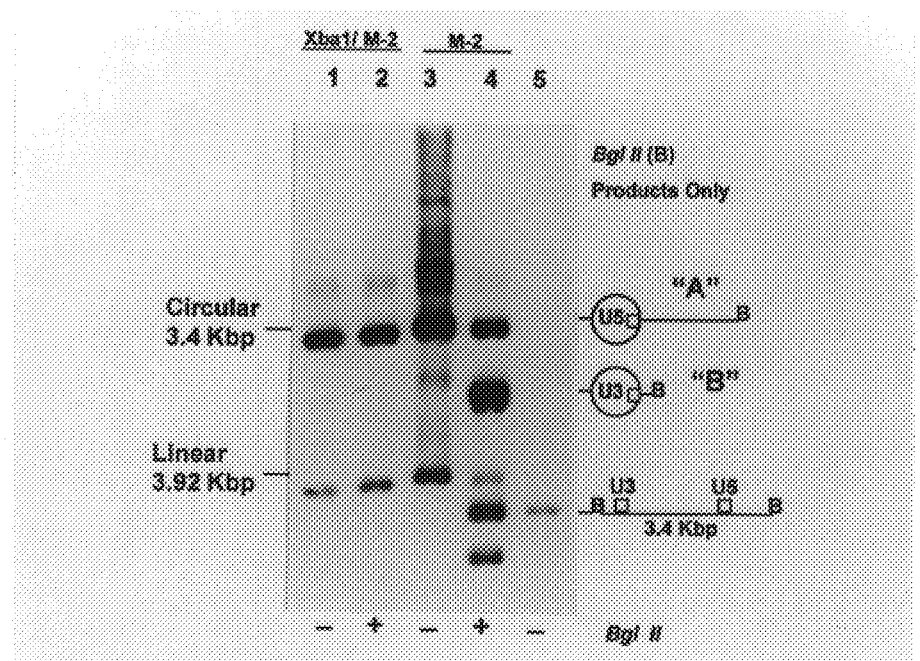

FIG. 3. Formation of IN/M-2 preintegration complexes and variation of donor to target ratios produces concerted M-2/pGEM recombinants. IN and M-2 were preincubated together on ice under standard reaction conditions at a molar ratio of 12, respectively. The donor (M-2 or XbaI truncated M-2) to target molar ratio was 1. The target was added just prior to incubation at 37° C. for 20 min. The reactions were processed and some were digested with Bg/ll (see bottom). The samples were subjected to electrophoresis on 1.5% agarose gels. The dried gel was exposed for 22 hr with a screen. Lane 5 contains a labeled 3.4 Kbp DNA marker.

Figure 4:
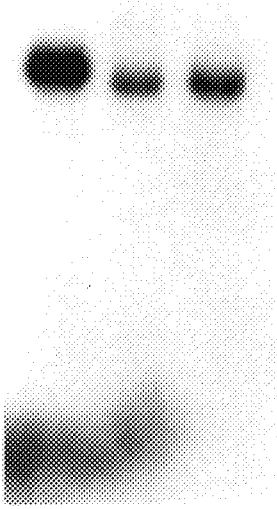

FIG. 4. Characterization of Bg/ll linearized 3.4 Kbp DNA derived from M-2/pGEM recombinants. Bg/ll digestion of all M-2/pGEM recombinants was performed as shown in FIG. 3, lane 4. Scale-up reactions were used to isolated the linearized 3.4 Kbp as described in Materials and Methods. Two thirds of the isolated DNA was ligated. The samples were subjected to 1.5% gel electrophoresis. Lane 1, one third unligated DNA; lane 2, one third ligated DNA; lane 3, one third ligated DNA but digested with Bg/ll. Linear and circular DNA size markers were used in separate lanes to verify the size of the labeled products.

Figure 5:
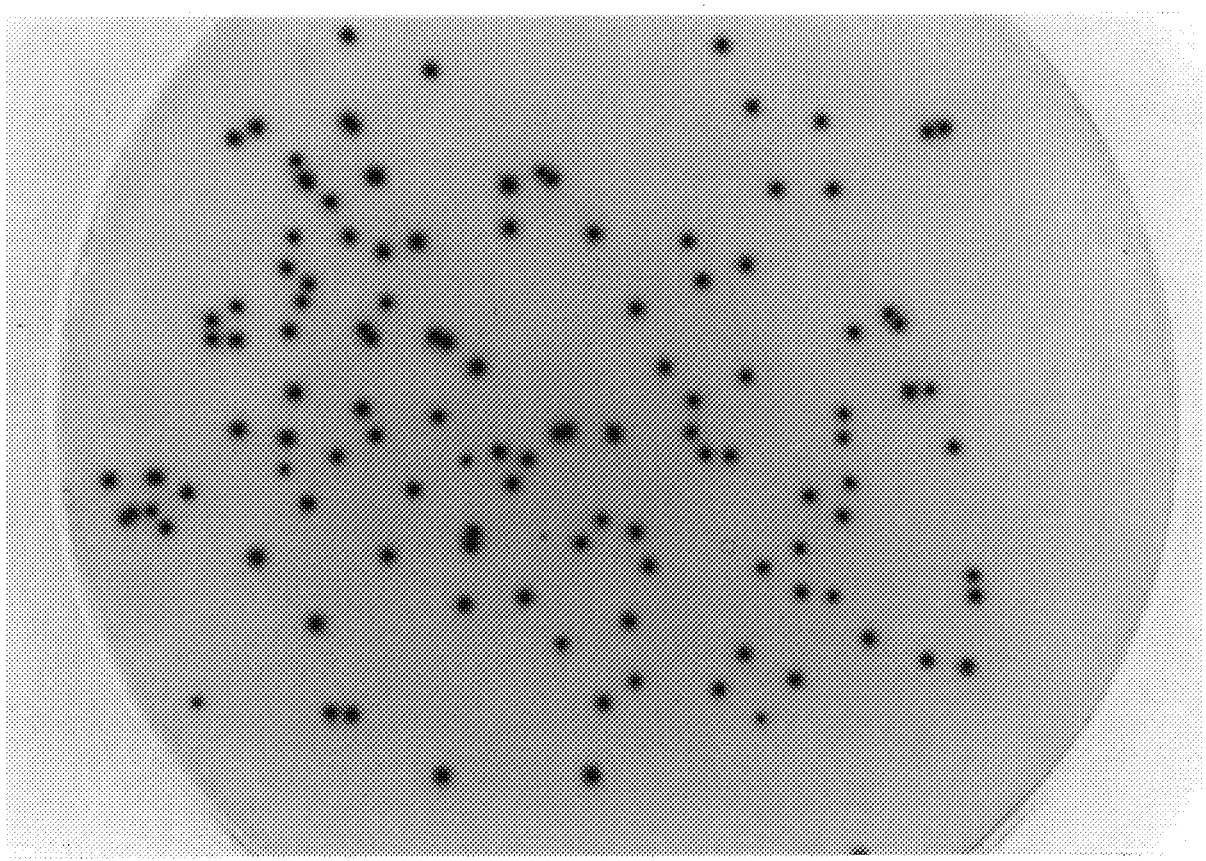

FIG. 5. Isolation of M-2/pGEM recombinants due to concerted integration on CA244 cells. The same Bg/ll linearized 3.4 Kbp shown in FIG. 4 was ligated and was used to transformed *E. coli* CA244 containing two amber mutations. The cells were grown as described in Materials and Methods and photographed after 62 hr of growth.

Figure 6:
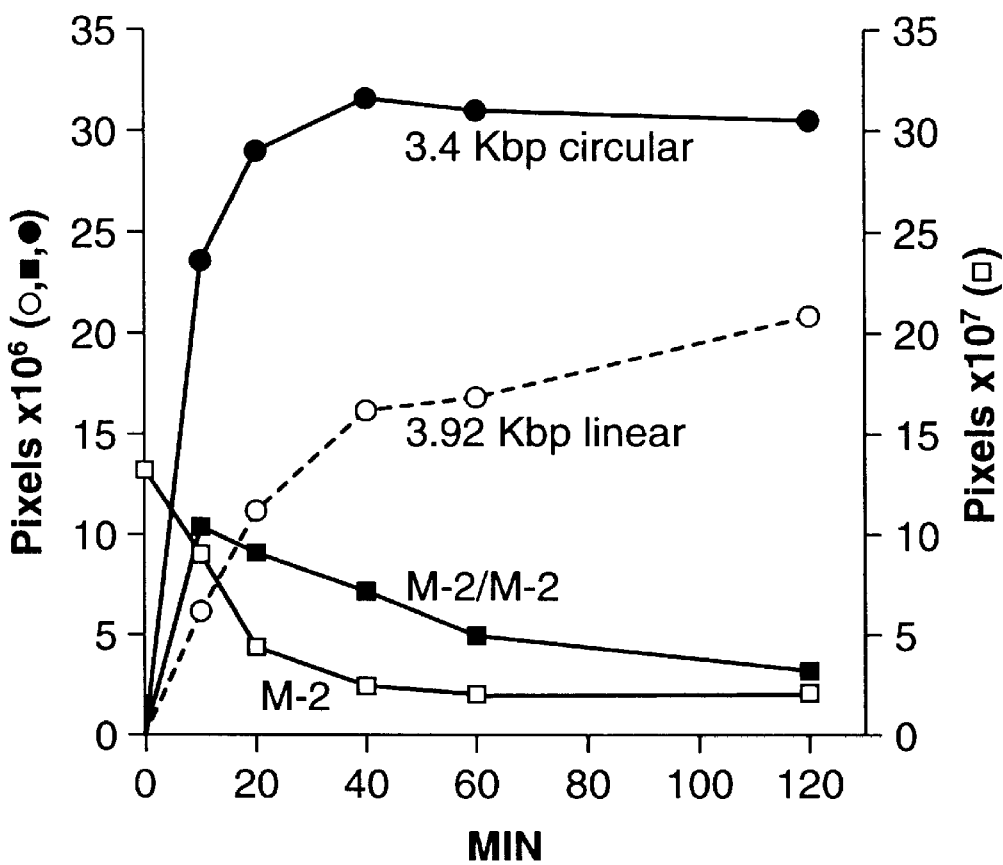
Figure 6:
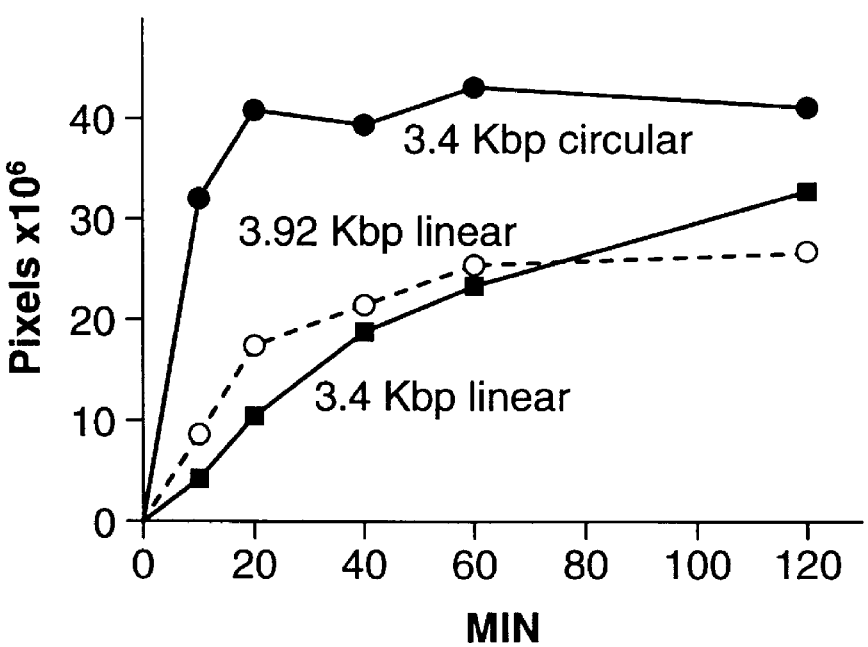

FIG. 6. Time course analysis of M-2/pGEM recombinant synthesis. (A) Standard reaction conditions were used with preincubation of M-2 with IN prior to incubation in the presence of pGEM. Aliquots were taken at the indicated times and the samples were subjected to electrophoresis on 1 % agarose gels. Upon drying, the gel was subjected to phospholmager analysis. The utilization of M-2 as donor and synthesis of the various recombinants was quantitated as pixels. (B) Aliquots of the above reactions were also analyzed on 1.5% agarose gels. Half of the samples were digested with Bg/ll prior to electrophoresis to quantitate Bg/ll linearized 3.4 kbp. See FIG. 8 for photograph of exposed x-ray films of the above reactions.

Figure 7:
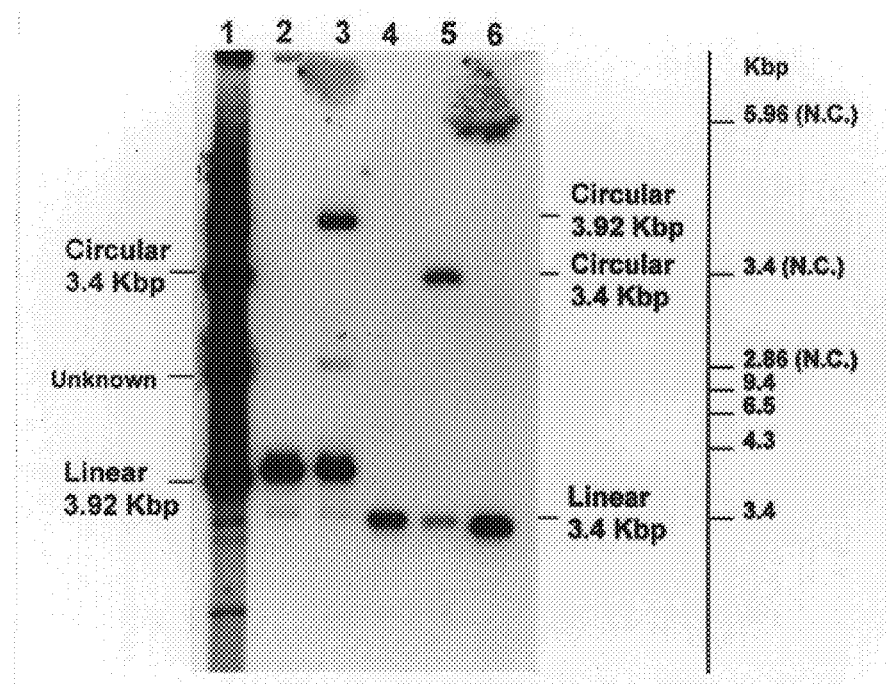

FIG. 7. Isolation and characterization of linear 3.92 Kbp DNA produced by two individual M-2 molecules per pGEM molecule. A scale-up reaction (lane 1) was employed to purify the 3.92 Kbp recombinant which is shown in lane 2. A portion of the purified DNA was ligated (lane 3) or digested with Bg/ll. The resulting Bg/ll linearized 3.4 Kbp DNA was purified (lane 4) and an then subjected to ligation (lane 5). Lane 6 contained 5'end labeled 3.4 Kbp DNA. The samples were analyzed on 1.5% agarose gels. The far right side identifies the location of various linear DNA markers.

Figure 8A:
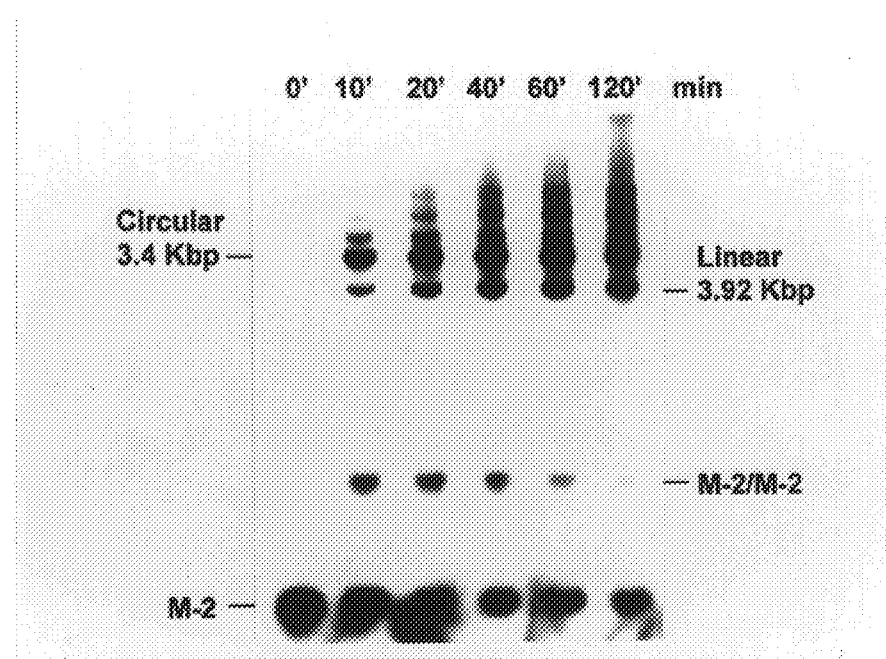
Figure 8B:
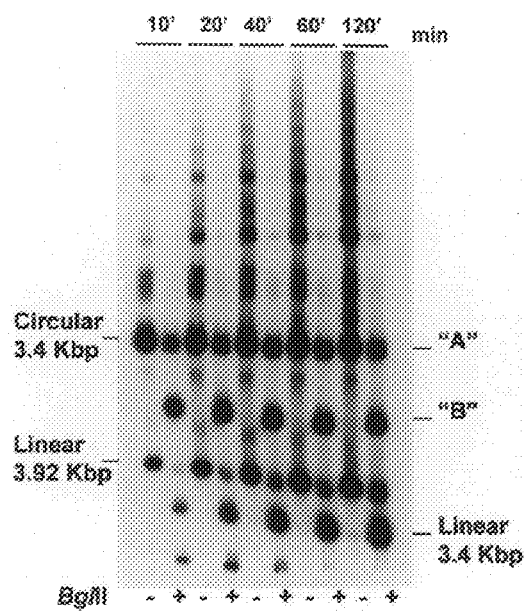

FIGS. 8A and 8B. Kinetics of M-2 utilization and synthesis of donor/donor and donor/target molecules. (A) Standard reaction conditions were used that included the preincubation of M-2 with IN. Equal aliquots were removed at the indicated times. They were processed and subjected to 1% agarose gel electrophoresis. The dried gel was exposed for 24 hr without a screen. The donor and M-2/M-2 and M-2/pGEM recombinants are identified. (B) The same samples were also subjected to 1.5% agarose gel electrophoresis with one half of each aliquot being digested with Bg/ll as indicated. The gel was exposed for 24 hr with a screen. The left side of the gel identifies M-2/pGEM recombinants while the right side identifies Bg/ll digested products. The bottom line indicates which samples were digested with Bg/ll. For the 10 min sample, 40% of the sample was lost prior to electrophoresis.

Figure 9:
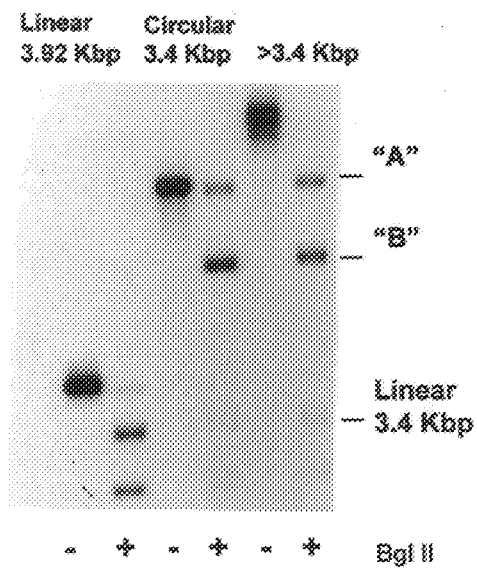

FIG. 9. Defining the origins of the Bg/ll linearized 3.4 Kbp DNA. The following M-2/pGEM recombinants (linear 3.92 Kbp, circular 3.4 Kbp, and >3.4 Kbp DNAs) were purified on 1.5% agarose gels. After isolation, an aliquot of each DNA was digested with Bg/ll and all of the samples were again subjected to gel electrophoresis. The right side of the gel identifies digestion products and the bottom line indicates which DNA were digested with Bg/ll. A total of 4% of the circular 3.4 Kbp recombinants are concerted events as defined by phosphoimager analysis.

Figure 10:
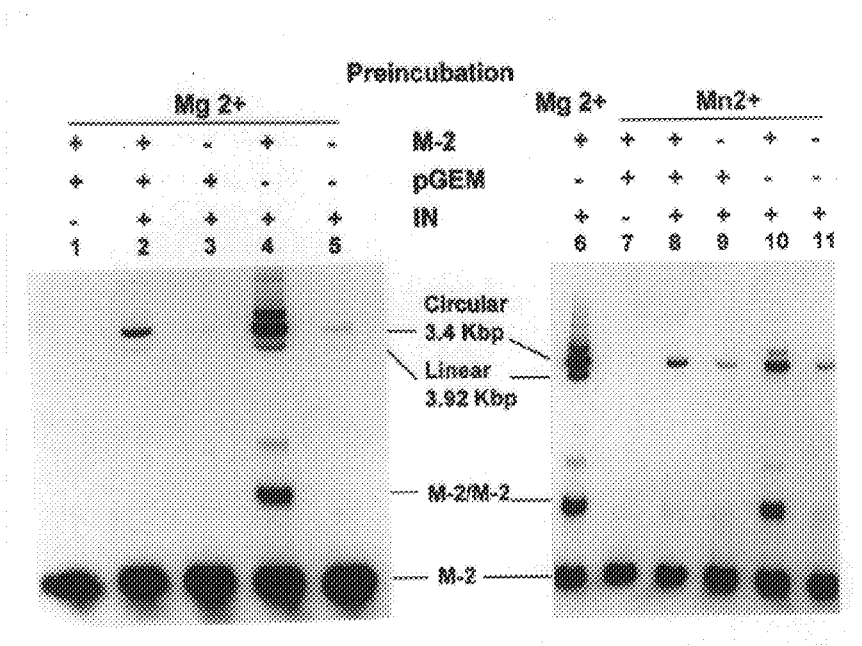

FIG. 10. Order of addition and divalent metal ion affects production of M-2/pGEM recombinants. Standard reaction conditions were employed throughout except for the presence or absence of IN, M-2, and pGEM in the preincubation mixture. Following preincubation on ice, the reactions were initiated by the addition of the missing reagent or reagents. Incubation was for only 10 min at 37° C. Lanes 1 to 6 and lanes 7 to 11 contained $Mg^{2+}$ (10 mM) and $Mn^{2+}$ (1 mM), respectively. Experiments in lanes 1 to 5 and lanes 6 to 11 were performed independently. The middle line indicates which reagents were present in the individual experiments and the various recombinants produced.

Figure 11:
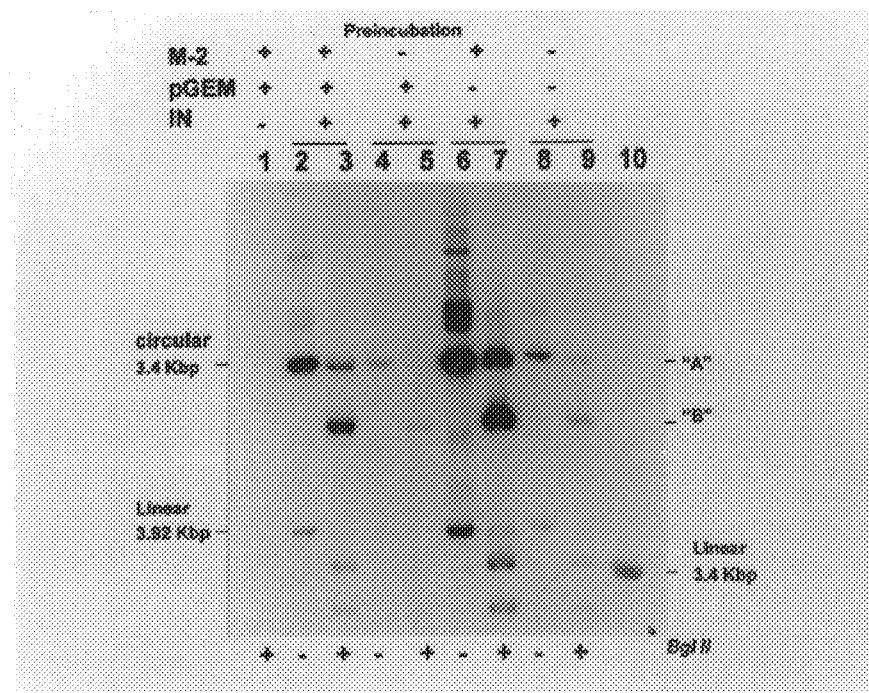

FIG. 11. Order of addition of donor and target affects the concerted integration reaction. Standard assay conditions in the presence of $Mg^{2+}$ were employed. The samples shown in FIG. 10 were grouped into pairs with one half of the sample digested with Bg/ll, followed by electrophoresis on 1.5% agarose gels. The left side of the Figure designates undigested products while the right side identifies digested products. Lane 1 contained no IN with the other lanes identifying what reagents were present in the preincubation mixtures. Lane 10 contained a linear 3.4 Kbp marker. The bottom line indicates which samples were digested with Bg/ll.

Figure 12:
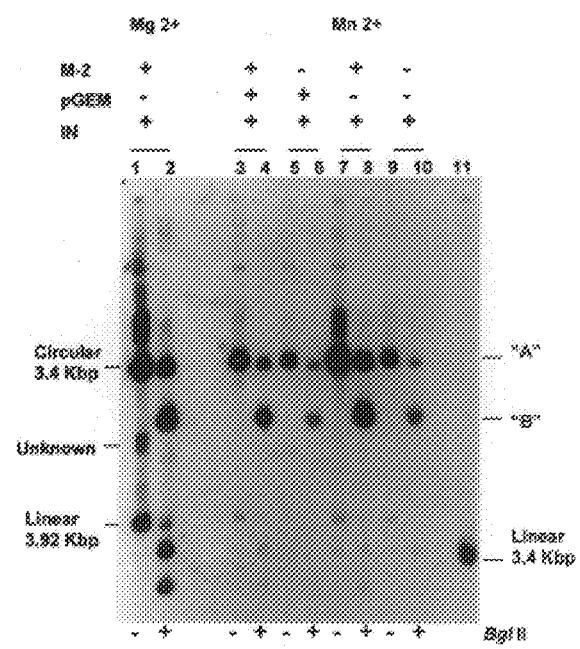

FIG. 12. Lack of concerted integration of M-2 into pGEM in the presence of $Mn^{2+}$. Standard reaction conditions were used except that 1 mM $Mn^{2+}$ was used. The samples shown in FIG. 10 were grouped into pairs with one half of the samples digested with Bg/ll, followed by electrophoresis on 1.5% agarose gels. The left side of the Figure identifies undigested products while the right side designates digested products. Lanes 1 and 2 contained $Mg^{2+}$ instead of $Mn^{2+}$ to serve as an identical control to lanes 7 and 8. The top lines indicates which reagents were present in the preincubation mixtures. Lane 11 contained a linear 3.4 Kbp marker. The bottom line identifies which samples were digested with Bg/ll.

Figure 13:
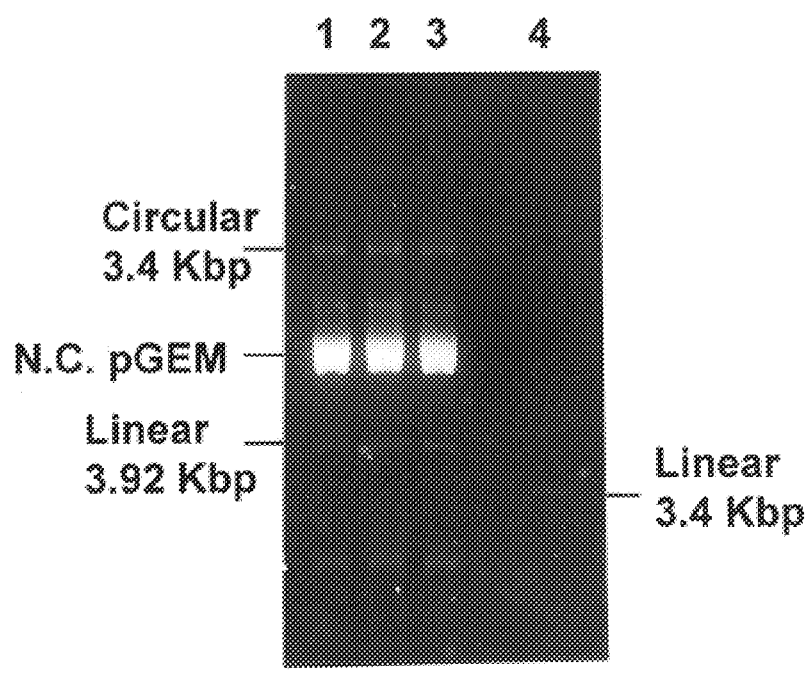

FIG. 13. Ethidium bromide staining of a scale-up M-2/pGEM integration reaction. Standard integration reaction conditions were used.

FIG. 14. The sequence of M-2 is SEQ ID NO: 1. The SEQ ID NO: 2, SEQ ID NO: 3, SEQ ID NO: 4, SEQ ID NO: 5, SEQ ID NO: 6 and SEQ ID NO: 7 are sequences of M-2 termini and PGEM DNA target. The U5 and U3 sequences of M-2 are covalently attached to the pGEM target, respectively, for three sequenced clones. The SEQ ID NO: 2 and SEQ ID NO: 3 are for the recombinant clone shown at the top of the figure, SEQ ID NO: 4 and SEQ ID NO: 5 are for the middle recombinant clone and SEQ ID NO: 6 and SEQ ID NO: 7 are for the bottom recombinant clone, respectively. Examples of sequenced M-2/pGEM recombinants that are the result of concerted integration.

FIG. 15. Production of concerted H-2/pGEM recombinants using HIV-1 virions. The same concerted integration event s shown in the avian system also ocrurs using HIV-1 virions, $Mg^{2+}$ and the appropriate HIV-1 donor molecule (H-2) that has the correct HIV-1 LTR termini. The reaction conditions are the same as described for the avian concerted integration reaction except non-ionic detergent lyzed HIV-1 virion were used for integrase activity. The appropriate labeled structures are indicated. Lane 1, no HIV-1 virions; lane 2, HIV-1 (1.67 $\mu$g) with H-2 donor; lane 3, HIV-1 with H-2 donor but digested with Bg/ll; Lane 4, linear 3.4 Kbp size marker.

PREFERRED EMBODIMENT OF THE INVENTION

The invention is further explained by referring to preferred embodiment and the following and examples.

This invention relates to the conditions necessary to reconstitute a viral nucleoprotein complex capable of efficiently performing the concerted integration reaction. IN purified from AMV is capable of the full-site integration reaction using a linear 3.4 Kbp plasmid-based virus-like substrate as donor and gtwes as target. The reaction required $Mg^{2+}$ and approximately 0.25% of the donor substrate was inserted into the target in a concerted fashion. The data demonstrated that AMV IN is capable of catalyzing the full-site reaction but conditions for formation of preintegration complexes capable of efficient concerted integration were not optimal.

To optimize conditions to investigate IN/donor preintegration complexes capable of concerted integration, the 3.4 Kbp donor molecule and the target were changed. The size of the donor was reduced to 528 bp, referred to as termed M-2 (FIG. 1A) to optimize the cyclization probability ( j factor)(Ref.1) of the molecule. A transient circle is an apparent necessity for concerted integration as well as for trimming of the viral genome by IN in vivo. The formation of DNA looped structures by AMV IN in the 3.4 Kbp donor molecule map to A/T rich regions (Ref.2). The ability of IN to form DNA looped structures may hinder the formation of preintegration complexes capable of the full-site reaction.

M-2 lacks A/T rich regions to overcome this problem. The target was changed to a small circular DNA (pGEM-3, 2,867 bp) to provide an easier analysis of IN/donor complexes and its interactions with target DNA.

The full-site integration reaction could occur via two pathways using the above substrates (FIG. 1). First, the termini of a single M-2 molecule can be inserted by IN into circular pGEM (FIG. 1B). Second, the termini of two individual M-2 molecules can be inserted in a concerted fashion at the same site into pGEM (FIG. 1D). The insertion of a single M-2 terminus by IN into pGEM producing a half-site integration reaction can also occur (FIG. 1C). M-2 contains a unique restriction site not found in the target molecule thereby permitting isolation and analysis of half-site and full-site integration recombinants by agarose gel electrophoresis (FIG. 1). M-2 also contained the supF gene that was used for genetic isolation of individual full-site recombinants to characterize the target site.

Bacteria and Plasmids.

The plasmid R35 ( Ref.2 ) was the source of the avian 65-bp LTR insert and the supF gene (469 bp). Both DNA fragments were used to reconstruct the M-2 donor fragment into pUCl9 (New England BioLabs). pGEM-3 was from Promega. *Escherichia coli* (strain CA244), that had amber mutations in the lacZ gene and for tryphotan biosynthesis, was obtain from the *E.coli* Genetic Stock Center at Yale University. CA244 cells transformed by M-2/pGEM recombinants or R-35 containing the supF gene were grown at 37° C. in M9 medium that contained autoclaved casamino acids (2 g/L), lactose (0.2%), 0.5 mM IPTG, 40 $\mu$g/ml X-Gal, and ampicillin (30 $\mu$g/ml).

Construction of donor M-2, SEQ ID. NO;1

The 65 bp LTR circle junction was recovered from R35 by EcoRI digestion. The isolated fragment was ligated and then digested by NdeI. The DNA was cloned into the NdeI site of pBR322 lacking its EcoRI site. A plasmid was selected that contained a single U3/U5 insert having NdeI termini and an internalized EcoRI site. The amplified DNA was digested with EcoRI and the supF gene was cloned into this site by blunt-end ligation. Digestion of this plasmid by NdeI yielded a 528 bp restriction fragment that contained U3 and U5 LTR termini and the internalized supF gene. This restriction fragment was termed M-2 ( FIG. 1) and served as a donor substrate. M-2 also contained the polylinker site derived from piAN7 that has unique BglII and XbaI sites. The XbaI site located near the U3 terminus of M-2 was used to create a donor molecule that lacked its U3 terminus but was similar in size to M-2. The XbaI/M-2 donor was use to help identify and characterize half-site M-2/pGEM recombinants. M-2 was subsequently cloned into the NdeI site of the high copy-number pUC19 for large scale isolation of the restriction fragment.

Labeling of M-2.

The supercoiled forms of pUC19 containing M-2 and pGEM were isolated by velocity sedimentation on sucrose gradients to remove any small size DNA or RNA fragments. M-2 was released from pUC19 by NdeI digestion and was isolated by low-m elt agarose gel electrophoresis. Following purification, M-2 was dephosphorlyated and 5' end labeled using γ-32P ATP and T4 polynucleotide kinase. The specific activity of M-2 was generally 5,000 to 10,000 cpm per ng of DNA. The pUC19 plasmid containing M-2 was also digested by Xbal and Ndel releasing M-2 lacking its U3 terminus (FIG. 1A). This fragment (490 bp) was labeled at both of its 5' ends as described above. Xbal digestion of M-2 removed the first two nucleotides of the adjacen t Bglll site.

Assay Conditions.

The standard reaction mixture contained 20 mm Tris-hydrochloride (pH 7.5), 5 mM dithiothreitol, 5 mM $MgCl_2$, 10% dimethyl sulfoxide, 0.05% Nonidet P-40, 5% polyethylene glycol, and 200 mM NaCl. The preincubation step included incubation of M-2 with IN at 0° C. for 10 min in 20 μl aliquots. The molar ratio of dimeric IN (33 ng) to M-2 (15 ng) was usually set at 12 unless otherwise indicated. The catalytic reaction was initiated by the addition of supercoiled pGEM followed by the immediate incubation at 37° C. The standard concentrations of labeled M-2 and pGEM were 15 ng and 100 ng, respectively. The molar ratio of M-2 to pGEM was 1. Scale-up reactions maintained the same molar ratios of enzyme to DNA substrates for isolation of various M-2/pGEM recombin ants. Some reaction conditions were modified as indicated in the text.

Analysis of M-2/pGEM recombinants.

After the integration reaction, each reaction was stop with sodium dodecyl sulfate and proteinase K at final concentrations of 1% and 1 mg/ml, respectively. The samples were further incubated at 37° C. for 2 hr and then subjected to phenol-chloroform (1:1) and ether extractions. The DNA was precipitated by ethanol. Aliquots of each sample were subjected to electrophoresis on 1 or 1.5% agarose gels which were dried and the radioactive products were quantitated by a Molecular Dynamics PhosphorImager. The dried gels were also exposed to X-ray films with or without an intensifying screen. For BglII restriction analysis of the M-2/pGEM recombinants, each 20 μl reaction mixture was digested by 12 units of BglII for 2 hr to ensure complete digestion. The samples were subjected to electrophoresis on 1.5% agarose gels in a Tris-borate-EDTA buffer with 0.5 μg/ml of ethidium bromide for 13 hr at 100 volts. The gels were dried and analyzed as described above. Linear DNA fragments (Boehringer Mannheim), pGEM, and R35(Ref.2) were used as unlabeled molecular weight markers. Linear R35 (3.4 Kbp) was 5' end labeled with γ-32P ATP and was used to identify the same size BglII linerarized M-2/pGEM recombinants which resulted from the concerted insertion of M-2 into pGEM.

Characterization of M-2/pGEM recombinants resulting from concerted integration events.

The 3.4 kbp BglII linearized DNA obtained from digestion of all of the M-2/pGEM recombinants was isolated from scale-up integration reactions. The BglII digested recombinants were subjected to electrophoresis on 1.5% agarose gels and the wet gel was exposed to X-ray film. The desired fragment was excised and electroeluted from the gel slice. The labeled DNA was purified by a Wizard PCR Prep column (Promega) and stored at −20° C. The purified DNA was ligated and analyzed by agarose gel electrophoresis or transformed into *E coli* HB101,*Epicuran Coli* Sure (Stratagene) or CA244 cells. Colonies were screened for plasmids that were analyzed by size, restriction enzymes, and DNA sequencing. Primers for sequencing were located within M-2 near both the U3 and U5 termini and were used to sequence the donor/target junctions. Sequencing was accomplished by the didexoxy method. The purified DNA was also examined by electron microscopy to determine the size and structure of the linearized DNA and other DNA structures as previously described ( Ref.2 ). Individual M-2/pGEM recombinants 13 (>3.4 Kbp circular DNA, 3.4 Kbp circular DNA , and linear 3.92 Kbp ) were also isolated and analyzed as described above.

Purification of integrase.

AMV IN was purified to near homogeneity as previously described ( Ref.2 ).

Parameters for production and physical quantitation of concerted integration events.

I wanted to devise a scheme which would permit the use of a simple approach to investigate concerted integration of a donor molecule into a DNA target. This scheme should allow an easy indepth examination of reaction conditions which promote full-site reactions. Such an approach is cartooned in FIG. 1. The linear donor molecule (M-2) has recessed U3 and U5 termini, is 528 bp in length which is optimal for forming transient circles , and has a unique BglII restriction site (FIG. 1A). Concerted integration of a single linear M-2 molecule into circular pGEM-3 (2,867 bp) by AMV IN would result in the formation of a 3.4 Kbp circle, which when digested by BglII, produces a 3.4 Kbp linear molecule (FIG. 1B). Half-site integration of M-2 into pGEM would result in a stick and ball structure also with a mass of 3.4 Kbp (FIG. 1C); BglII digestion of this half-site recombinant would result in the formation of two different stick and ball structures ( "A" or "B"), depending on whether the U3 or U5 terminus was inserted. Prior XbaI digestion of M-2 (FIG. 1A) would produce a molecule capable of only producing U5 half-site recombinants (stick and ball structure "A") whose mass is 3.36 Kbp (FIG. 1C). Lastly, concerted integration could also result from a single insertion event involving two separate M-2 molecules (or 2 XbaI/M-2 molecules) into circular pGEM at one site (FIG. 1D). The integration of 5' end labeled M-2 or XbaI digested M-2 into circular pGEM can be easily followed by restriction enzyme digestion and agarose gel electrophoresis.

IN/M-2/pGEM preintegration complexes.

I wanted to test the above protocol (FIG. 1) for the production of concerted integration recombinants. I first tested reaction conditions which were conducive for formation of complexes capable of performing the concerted integration reaction employing a linear 3.4 Kbp donor and λgtWES. IN, M-2, and pGEM were preincubated together on ice for 10 min with Mg2+ prior to incubation at 37○ (FIG. 2). The donor to target molar ratio was 16 and the IN dimer to M-2 molar ratio was 12. The reactions were stopped at the indicated times and were analyzed by gel electrophoresis on 1.5% agarose (FIG. 2, lanes 2 and 3). Only two major labeled M-2/pGEM products were formed, one which comigated with a nicked circular 3.4 Kbp marker and the other group migrating slightly slower. Electron microscopy of both DNA species confirmed that the majority (~97%) of the 3.4 Kbp M-2/pGEM recombinants were of the ball and single stick model ("A", FIG. 1C) and the slower migrating group of recombinants were circular pGEM with two or more independent M-2 inserts (data not shown). These structural data were confirmed using XbaI digested M-2, which lacks the U3 terminus (FIG. 1). Only single insertion events of U5 ends of XbaI/M-2 into pGEM migrating with a mass of 3.36 Kbp were observed by gel electrophoresis (FIG. 2, lanes 9 and 10) or by electron microscopy (data not shown).

Digestion of the M-2/pGEM recombinants containing circles by BglII should result in the cleavage of all BglII sites regardless of whether they are half-site or full-site recombinants. With all half-site reactions, one-half of radioactivity will be lost upon BglII digestion while no radioactivity would be lost by BglII digestion of full-site reactions because no 5' -end labeled termini are lost(FIGS. 1B and 1C). Two major products were produced by BglII digestion of M-2/pGEM recombinants formed under these above conditions (FIG. 2, lanes 4 and 5). The slowest moving DNA migrated with a mass of 3.4 Kbp ("A" product) and the fastest moving DNA ("B" product) nearly comigrated with nicked circular pGEM (2.86 Kbp). The "A" and "B" products derived by BglII digestion of M-2/pGEM recombinants would be the result of half-site U5 and U3 insertions, respectively. As expected, digestion of XbaI/M-2 recombinants with BglII (FIG. 2, lanes 7 and 8) did not alter the migration of these recombinants nor identified any recombinants containing U3 insertions.

The digestion of M-2/pGEM recombinants produced under these reaction conditions did not reveal a significant quantity of linear 3.4 Kbp product suggesting that few full-site M-2/pGEM recombinants were formed (FIG. 2, lanes 4 and 5). The 3.4 Kbp donor molecule served as an identical molecular weight marker for the expected BglII linearized M-2/pGEM recombinant (FIG. 2, lane 6). Prolonged exposure of this gel did result in a minor product comigrating at 3.4 Kbp (FIG. 2, lanes 4 and 5).

IN/M-2 preintegration complexes.

To increase the efficiency of the full-site integration reaction, several reactants and procedures were modified. The formation of IN/M-2 preintegrations complexes were allowed to occur on ice prior to the addition of target. The molar ratio of M-2 to PGEM was decreased to 1 from 16. The IN to M-2 molar ratio was held constant at 12. Preincubation of IN/M-2 together prior to addition of target and subsequent incubation at 37° C. for 30 min resulted in the formation of three major M-2/pGEM recombinant species (FIG. 3,lanes 3). The two slowest migrating M-2/pGEM recombinants in these lanes of FIG. 3 were previously described (FIG. 2, lanes 2 and 3) and the fastest moving M-2/pGEM recombinant is presumed to be 3.92 Kbp linear DNA (FIG. 1D) . I will address this linear 3.92 Kbp M-2/pGEM recombinant later. BglII digestion of the reaction products observed in lane 3 of FIG. 3 resulted in the formation of a labeled product (lane 4) which comigrated with the 3.4 Kbp linear marker (lane 5). Quantitation using PhosphoImager analysis showed that the linearized M-2/pGEM recombinant (FIG. 3, lane 4) represented 22% of the radioactively associated with the non-digested BglII 3.4 Kbp and 3.92 Kbp M-2/pGEM recombinants(lane 3).

BglII digestion of M-2/pGEM recombinants also reaffirmed early data on the preference of U3 over U5 termini for both the trimming and strand transfer reactions by AMV IN by a 2 to 1 margin. This same U3 over U5 preference was observed by BglII digestion of either M-2/pGEM recombinants when either circles (FIG. 3, lane 4, products "A" and "B").

Physical and genetic analysis of concerted M-2/pGEM recombinants.

I needed to confirm that the linearized 3.4 Kbp M-2/pGEM recombinants were the result of a full-site integration reaction. Several 30 min scale-up reactions were performed and the samples were subjected to BglII digestion. The linearized 3.4 Kbp DNA was identified on wet 1.5% agarose gels by autoradiography and was eluted and purified. The 3.4 Kbp recombinant was ligated and then analyzed again by 1.5% agarose gel electrophoresis (FIG. 4, lanes 2 and 3). The ligated DNA comigated with the original circular 3.4 Kbp molecule (FIG. 4,lane 1). In three separate experiments, the maximum amount of the circular 3.4 Kbp product produced by ligation was 75% suggesting that some of the DNA ends were damaged upon elution and purification of the linearized DNA. Digestion of the ligated 3.4 Kbp circle by BglI, which only cuts pGEM and not M-2, again resulted in the production of only linear 3.4 Kbp DNA (data not shown).

To further establish that only linear recombinant DNA is present in the BglII linearized 3.4 Kbp band, the purified DNA was analyzed by electron microscopy. Counting 200 molecules, 70% of the molecules were linear structures 3.4 Kbp +150 bp in length, 1% were branched structures of the same size,15% were linear molecules of various sizes and 15% were circles of 2.86 Kbp in length. The various smaller size linear molecules probably represent degraded 3.4 Kbp DNA. The 2.86 Kbp circular DNA is unused pGEM (>96% of the target DNA is not used in the 30 min reactions as observed by ethidium bromide staining of DNA). The contaminating pGEM represents a very minor population of topological forms of PGEM induced by the presence of ethidium bromide in the 1.5% agarose gels that comigrates with the labeled 3.4 Kbp linearized DNA.

Does the linearized 3.4 Kbp recombinant DNA represent true concerted integration events? The only definite way to establish that each recombinant contains the correct host duplicated site that is observed upon concerted integration in vivo is by the genetic selection of individual recombinants. The purified 3.4 Kbp BglII linearized DNA (FIG. 4) was ligated and transformed into $E.$ $coli$ (HB101, Epicuran Coli Sure cells, or CA244). Screening of individual colonies demonstrated that 5 to 10% of the plasmids were 3.4 Kbp in length when either HB101 or Sure cells were used as hosts. Also, fill-in and repair of the ligated 3.4 Kbp DNA by $E$ $coli$ DNA polymerase I before transformation did not increase the percentage of rescued 3.4 Kbp plasmids.The rest of the plasmids were 2.86 Kbp in length. Restriction enzyme analysis of all the rescued plasmids demonstrated that the 3.4 Kbp DNA were concerted integration products and the 2.86 Kbp DNA was pGEM. DNA sequence analysis of 20 recombinants of 3.4 kbp in length demonstrated that all of them had the correct avian duplication host size (18 six bp; 1 five bp; and 1 seven bp). These above data demonstrated that the 3.4 Kbp M-2/pGEM recombinants were the products of full-site integration events. The observation that only 5 to 10% of the rescued plasmid were the correct recombinants suggests that the ligation of the 3.4 Kbp was incomplete (FIG. 4) and unused pGEM target was present as demonstrate by electron microscopy.

To decrease the pGEM background in the genetic assay, we transformed the ligated 3.4 Kbp DNA into CA244 cells which have amber mutations in the lacZ gene and for tryptophan biosynthesis. M-2 contains the supF gene which when inserted into pGEM in a concerted matter (FIG. 1B) would permit the replication of this recombinant plasmid but not pGEM in CA244 cells. Transformation of CA244 resulted in the production of only blue colonies (FIG. 5) and all of the rescued plasmids were 3.4 Kbp in length. DNA sequence of eight plasmids verified that they were all the result of concerted integration events.

Characterization of the IN/M-2 complexes capable of concerted integration.

I wanted to compare the synthesis rate of the concerted integration events with respect to all other half-site reactions and the utilization of the input M-2 substrate (FIG. 6). Standard preincubation of IN/M-2 in the present of Mg2+ prior to the synaptic reaction with pGEM was employed (FIG. 3). Aliquots were removed at the indicated times and the DNA samples were analyzed by 1% agarose gel electrophoresis to quantitate disappearance of input substrate and formation of all recombinants (See FIG. 8 as an example). An equal aliquot of each sample was also digested or not digested with BglII to quantitate the concerted integration reaction (FIG. 6A). As shown in FIG. 6B, most of the catalysis occurs in the first 40 min of incubation at 37° C. Eighty percent of the input M-2 substrate is used (data not shown) and both the synthesis of the 3.4 Kbp circular and linear DNAs are leveling off. Maximal insertion of M-2 into other M-2 molecules occurs earlier at 20 min followed by their disappearance with further incubation. These presumed half-site M-2/M-2 recombinants were probably subjected to the disintegration reaction which AMV IN in the presence of Mg2+ is capable of performing using appropriate disintegration substrates composed of oligonucleotides (data not shown). Further analysis of all the M-2/pGEM recombinants by Bglll digestion and 1.5% gel electrophoresis demonstrated that the concerted integration events (linearized 3.4 Kbp DNA) occurred at a linear rate for approximately 40 min but does not level off entirely (FIG. 6A and 6B). After 2h of incubation, the 3.4 Kbp linearized DNA represents 80% of the 3.4 Kbp circle population. The linearized 3.4 Kbp DNA derived from the reaction at these latter times has the same properties as shown previously for linearized 3.4 Kbp produced at 30 min.

Several of the major components in a standard reaction mixture were separately removed to determine whether individual components affected the full-site integration reaction. The reactions were for 30 min at 370 ° C. with the standard 10 min preincubation of IN/M-2 on ice. The samples were subjected to Bglll digestions , gel electrophoresis, and PhosphorImager analysis. The individual removal of Nonidet P-40 appear to had little affect on the full-site and half-site reactions into pGEM. Both of these catalytic reactions were influenced equally by DMSO with maximum catalysis occurring between 10 and 15% DMSO. There was an approximate 3 to 4 fold increase in all M-2/pGEM recombinants, including full-site recombinants, above those observed with no DMSO present. PEG also was necessary for maximum stimulation. The addition of glycerol(up to 10%) to the standard reaction mixture did not affect the integration reaction.

While the present invention has been described by reference to preferred embodiment, it should be understood that modifications and variations of the invention may be derived without departing from the spirit of the invention.

References:
1. Hochschild, A. 1991. Detecting cooperative protein-DNA interactions and DNA loop formation by footprinting. Methods of Enzymology 208:343-361.
2. Grandgenett, D. P., R. Inman, A. Vora, and M. Fitzgerald. 1993. Comparison of DNA binding and integration half-site selection by avian myeloblastosis virus integrase. J. Virology 67: 2628-26

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 491 base pairs
        ( B ) TYPE: nucleic acid
        ( C ) STRANDEDNESS: double
        ( D ) TOPOLOGY:linear ( i i ) MOLECULE TYPE: other nucleic acid ( i i i ) HYPOTHETICAL: no ( i v ) ANTI-SENSE: no ( v i ) ORIGINAL SOURCE: Combination of avian or HIV-1 retrovirus
                DNA and piAN7 plasmid.

( v i i ) IMMEDIATE SOURCE: Same as in 2,vi.

( i x ) FEATURE:
        ( D ) OTHER INFORMATION: A linear double-standed DNA,termed M-2
            in the original application. Contains amber supressor
            sequences and restriction enzyme sites. Termini contain
            retrovirus long terminal repeat sequences that the viral
            integrase uses for concerted integration.

( x i ) SEQUENCE DESCRIPTION: SEQ ID NO:1:

```
TATGAAGCCT    TCTGCTTCAT    GCAGGTGCTC    GTAGTCGAAT    TAGCTTGCGT         50

TGCTGGCGTT    TTTCCATAGG    CTCCGCCCCC    CTGACGAGCA    TCACAAAAAT        100

CGACGCTCAA    GTCAGAGGTG    GCGAAACCCG    ACAGGACTAT    AAAGATACCA        150

GGCATTACCC    GTCAGAAAAA    AAGGATCTCA    AGAAGATCCT    TTGATCTTTT        200

CTACGGGGTC    TGAACGGATC    TCAATTCTTT    CGGACTTTTG    AAAGTGATGG        250

TGGTGGGGGA    AGGATTCGAA    CCTTCGAAGT    CGATGACGGC    AGATTTAGAG        300

TCTGCTCCCT    TTGGCCGCTC    GGGAACCCCA    CCACAGGTAA    TGCTTTTACT        350
```

| | | | | | |
|---|---|---|---|---|---|
| GGCCTGCTCC | TTATCGGGAA | GCGGGGCGCA | TCATATCAAA | TGACGCGCCG | 400 |
| CTGTAAAGTG | TTACGTTGAG | AAAGAATTCC | CGGGGATCCG | TCGACCTGCA | 450 |
| GATCTCTAGA | AGCTAATTCA | AGAGTATTGC | ATAAGACTAC | A | 491 |

( 2 ) INFORMATION FOR SEQ ID NO:2:

( i ) SEQUENCE CHARACTERISTICS:
        ( A ) LENGTH: 15 bases
        ( B ) TYPE: nucleic acid
        ( C ) STRANDEDNESS: double
        ( D ) TOPOLOGY:linear ( i i ) MOLECULE TYPE: other nucleic acid ( i i i ) HYPOTHETICAL: no ( i v ) ANTI-SENSE: no ( v i ) ORIGINAL SOURCE: Combination of avian or HIV-1 retrovirus
        DNA, piAN7 plasmid and pGEM plasmid.

( v i i ) IMMEDIATE SOURCE: Same as in 2,vi.

( i x ) FEATURE:
        ( D ) OTHER INFORMATION: The sequence is the bottom strand of
        M-2 U5 and the pGEM target of the top clone shown in
        Figure 14 of original application.

( x i ) SEQUENCE DESCRIPTION: SEQ ID NO:2:

CTTCATACTG    GGCTG                       15

( 2 ) INFORMATION FOR SEQ ID NO:3:

( i ) SEQUENCE CHARACTERISTICS:
        ( A ) LENGTH: 15 bases
        ( B ) TYPE: nucleic acid
        ( C ) STRANDEDNESS: double
        ( D ) TOPOLOGY:linear ( i i ) MOLECULE TYPE: other nucleic acid ( i i i ) HYPOTHETICAL: no ( i v ) ANTI-SENSE: no ( v i ) ORIGINAL SOURCE: Combination of avian or HIV-1 retrovirus
        DNA, piAN7 plasmid and pGEM plasmid.

( v i i ) IMMEDIATE SOURCE: Same as in 2,vi.

( i x ) FEATURE:
        ( D ) OTHER INFORMATION: The sequence is the top strand of
        M-2 U3 and the pGEM target of the top clone shown in
        Figure 14 of original application.

( x i ) SEQUENCE DESCRIPTION: SEQ ID NO:3:

CTACACCAGT    AGTAG                        15

( 2 ) INFORMATION FOR SEQ ID NO:4:

( i ) SEQUENCE CHARACTERISTICS:
        ( A ) LENGTH: 15 bases
        ( B ) TYPE: nucleic acid
        ( C ) STRANDEDNESS: double
        ( D ) TOPOLOGY:linear ( i i ) MOLECULE TYPE: other nucleic acid ( i i i ) HYPOTHETICAL: no ( i v ) ANTI-SENSE: no ( v i ) ORIGINAL SOURCE: Combination of avian or HIV-1 retrovirus -continued DNA. piAN7 plasmid and pGEM plasmid.

(vii) IMMEDIATE SOURCE: Same as in 2,vi.

(ix) FEATURE:
(D) OTHER INFORMATION: The sequence is the bottom strand of M-2 U5 and the pGEM target of the middle clone shown in Figure 14 of original application.

(xi) SEQUENCE DESCRIPTION: SEQ ID NO:4:

CTTCAATATG AGTAA 15

(2) INFORMATION FOR SEQ ID NO:5:

(i) SEQUENCE CHARACTERISTICS:
(A) LENGTH: 15 bases
(B) TYPE: nucleic acid
(C) STRANDEDNESS: double
(D) TOPOLOGY:linear (ii) MOLECULE TYPE: other nucleic acid (iii) HYPOTHETICAL: no (iv) ANTI-SENSE: no (vi) ORIGINAL SOURCE: Combination of avian or HIV-1 retrovirus DNA, piAN7 plasmid and pGEM plasmid.

(vii) IMMEDIATE SOURCE: Same as in 2,vi.

(ix) FEATURE:
(D) OTHER INFORMATION: The sequence is the top strand of M-2 U3 and the pGEM target of the middle clone shown in Figure 14 of original application.

(xi) SEQUENCE DESCRIPTION: SEQ ID NO:5:

CTACACTCAT ATATA 15

(2) INFORMATION FOR SEQ ID NO:6:

(i) SEQUENCE CHARACTERISTICS:
(A) LENGTH: 15 bases
(B) TYPE: nucleic acid
(C) STRANDEDNESS: double
(D) TOPOLOGY:linear (ii) MOLECULE TYPE: other nucleic acid (iii) HYPOTHETICAL: no (iv) ANTI-SENSE: no (vi) ORIGINAL SOURCE: Combination of avian or HIV-1 retrovirus DNA. piAN7 plasmid and pGEM plasmid.

(vii) IMMEDIATE SOURCE: Same as in 2,vi.

(ix) FEATURE:
(D) OTHER INFORMATION: The sequence is the bottom strand of M-2 U5 and the pGEM target of the bottom clone shown in Figure 14 of original application.

(xi) SEQUENCE DESCRIPTION: SEQ ID NO:6:

CTTCAACCAT TCCTT 15

(2) INFORMATION FOR SEQ ID NO:7:

(i) SEQUENCE CHARACTERISTICS:
(A) LENGTH: 15 bases
(B) TYPE: nucleic acid
(C) STRANDEDNESS: double
(D) TOPOLOGY:linear -continued (ii) MOLECULE TYPE: other nucleic acid (iii) HYPOTHETICAL: no (iv) ANTI-SENSE: no (vi) ORIGINAL SOURCE: Combination of avian or HIV-1 retrovirus
         DNA, piAN7 plasmid and pGEM plasmid.

(vii) IMMEDIATE SOURCE: Same as in 2,vi.

(ix) FEATURE:
         (D) OTHER INFORMATION: The sequence is the top strand of
             M-2 U3 and the pGEM target of the bottom clone shown in
             Figure 14 of original application.

(xi) SEQUENCE DESCRIPTION: SEQ ID NO:7:

CTACAAATGG    TGCAA    15

What I claim my invention is:

1. An in vitro method for concerted integration of donor DNA molecules into target DNA molecules using a retroviral integrase, comprising, in order, the following steps:
   (a) incubating a first reaction mixture, comprising a suitable reaction buffer, the donor DNA molecules, and the retroviral integrase, to form preincubation complexes between the donor DNA molecules and molecules of retroviral integrase; and
   (b) introducing target DNA molecules into the first reaction mixture to form a second reaction mixture and incubating the second reaction mixture, such that the donor DNA molecules are integrated into the target DNA molecules.

2. The method according to claim 1 wherein the donor DNA molecules comprise at least one unique restriction site not present in the target DNA molecules.

3. The method according to claim 1 wherein the donor DNA molecules comprise at least one unique genetic marker not present in the target DNA molecules.

4. The method according to claim 1 wherein the reaction buffer contains at least one of NaCl, $MgCl_2$, or dithiothreitol.

5. The method according to claim 1 wherein the reaction buffer contains dimethyl sulfoxide.

6. The method according to claim 1 wherein the target DNA molecules are circular.

* * * * *